US005563031A

United States Patent [19]

Yu

[11] Patent Number: 5,563,031
[45] Date of Patent: Oct. 8, 1996

[54] HIGHLY STABLE OXIDATIVE COUPLING DYE FOR SPECTROPHOTOMETRIC DETERMINATION OF ANALYTES

[75] Inventor: Yeung S. Yu, Pleasanton, Calif.

[73] Assignee: LifeScan, Inc., Milpitas, Calif.

[21] Appl. No.: 302,575

[22] Filed: Sep. 8, 1994

[51] Int. Cl.$^6$ .............................. C12Q 1/00; C12Q 1/54; G01N 33/00; G01N 21/00
[52] U.S. Cl. .................. 435/4; 435/14; 435/28; 435/25; 436/94; 436/530; 422/57; 422/56; 422/55; 422/82.09; 422/78; 422/79
[58] Field of Search .................. 435/4, 14, 28, 435/25; 436/95, 94, 530; 422/82.09, 78, 79, 57, 56, 55

[56] References Cited

U.S. PATENT DOCUMENTS

| | | | |
|---|---|---|---|
| 3,552,928 | 1/1971 | Fetter | 23/253 |
| 3,980,437 | 9/1976 | Kishimoto et al. | 23/253 TP |
| 3,992,158 | 11/1976 | Przybylowicz et al. | 23/253 TP |
| 4,042,335 | 8/1977 | Clement | 23/253 TP |
| 4,119,405 | 10/1978 | Lam | 435/14 |
| 4,125,372 | 11/1978 | Kawai et al. | 422/82.05 |
| 4,144,306 | 3/1979 | Figueras | 422/56 |
| 4,255,384 | 3/1981 | Kitajima et al. | 422/57 |
| 4,258,001 | 3/1981 | Pierce et al. | 422/56 |
| 4,292,272 | 9/1981 | Kitajima et al. | 422/57 |
| 4,452,887 | 6/1984 | Kitajima et al. | 435/14 |
| 4,509,859 | 4/1985 | Markart et al. | 422/82.05 |
| 4,592,893 | 6/1986 | Poppe et al. | 422/58 |
| 4,682,895 | 7/1987 | Costello | 422/82.09 |
| 4,714,874 | 12/1987 | Morris et al. | 324/65 |
| 4,729,950 | 3/1988 | Kricka et al. | 435/28 |
| 4,774,192 | 9/1988 | Terminiello et al. | 436/530 |
| 4,790,979 | 12/1988 | Terminiello et al. | 422/56 |
| 4,816,224 | 3/1989 | Vogel et al. | 422/55 |
| 4,935,346 | 6/1990 | Phillips et al. | 435/14 |
| 4,978,503 | 12/1990 | Shanks et al. | 422/82.09 |
| 4,994,238 | 2/1991 | Daffern et al. | 422/56 |
| 5,029,583 | 7/1991 | Meserol et al. | 422/82.09 |
| 5,037,614 | 8/1991 | Makita et al. | 422/82.09 |
| 5,059,394 | 10/1991 | Phillips et al. | 435/14 |
| 5,082,516 | 1/1992 | Akao et al. | 422/82.09 |
| 5,084,382 | 1/1992 | Frey et al. | 435/28 |
| 5,095,025 | 3/1992 | Tanaka et al. | 514/367 |
| 5,095,026 | 3/1992 | Schoenwald et al. | 514/367 |
| 5,120,507 | 6/1992 | Sano et al. | 436/94 |
| 5,167,145 | 12/1992 | Butler et al. | 422/82.05 |
| 5,174,963 | 12/1992 | Fuller et al. | 422/57 |

. (List continued on next page.)

FOREIGN PATENT DOCUMENTS

| | | | |
|---|---|---|---|
| 0243126 | 10/1987 | European Pat. Off. . | |
| 0248312 | 12/1987 | European Pat. Off. . | |
| 0456098A2 | 11/1991 | European Pat. Off. | G01N 33/52 |
| 0555045 | 8/1993 | European Pat. Off. . | |
| 0574134A2 | 12/1993 | European Pat. Off. | G01N 33/52 |
| 4035052A1 | 11/1989 | Germany . | |
| 938029 | 8/1961 | United Kingdom . | |
| 1037155 | 7/1966 | United Kingdom . | |
| 2090659 | 7/1982 | United Kingdom | G01N 33/48 |
| 94/18559 | 8/1994 | WIPO | G01N 33/52 |

OTHER PUBLICATIONS

Chem. Abstracts No. 104: 99566 (1985).
Azo Dyes by Oxidative Coupling, VIII*, S. Hunig and Kobrich, Liebigs Ann. Chem. 617, 216 (1958).
Mechanism for Preventing Bending of Speciment for Urine; Japanese Patent Appl 2–233741, Sep. 4, 1990.
New Contributions to the Optics of Intensely Light–Scattering Materials, part I; Journal of Optical Society of America, vol. 38, No. 5, May 1948, pp. 448–457.

*Primary Examiner*—John Kight
*Assistant Examiner*—Louise N. Leary

[57] ABSTRACT

A dye couple compound is provided for use in a test device containing a reagent system for detecting the presence or quantity of an analyte in a sample. The reagent system comprises one or more enzymes which, in the presence of the analyte, produce an oxidizing agent in quantities indicative of the quantity of analyte in the sample. The compound of choice is meta[3-methyl 2-benzothiazolinone hydrozone] N-sulfonyl benzenesulfonate monosodium.

8 Claims, 1 Drawing Sheet

U.S. PATENT DOCUMENTS

| | | | |
|---|---|---|---|
| 5,179,005 | 1/1993 | Phillips et al. | 436/63 |
| 5,192,502 | 3/1993 | Attridge et al. | 422/57 |
| 5,211,914 | 5/1993 | Vogel et al. | 422/56 |
| 5,215,890 | 6/1993 | Theodoropulos et al. | 435/28 |
| 5,232,668 | 8/1993 | Grant et al. | 422/82.09 |
| 5,236,940 | 8/1993 | Audiau et al. | 514/367 |
| 5,246,858 | 9/1993 | Arbuckle et al. | 435/4 |
| 5,252,293 | 10/1993 | Drbal et al. | 435/4 |
| 5,277,870 | 1/1994 | Fuller et al. | 435/4 |
| 5,304,468 | 4/1994 | Phillips et al. | 435/14 |
| 5,306,623 | 4/1994 | Kiser et al. | 435/14 |

HIGHLY STABLE OXIDATIVE COUPLING DYE FOR SPECTROPHOTOMETRIC DETERMINATION OF ANALYTES

TECHNICAL FIELD

The present invention relates to a test device and method for the colorimetric determination of chemical and biochemical components (analytes) in aqueous fluids, such as whole blood, and, more particularly, to a dye couple for use in such device and method.

BACKGROUND ART

The quantification of chemical and biochemical components in colored aqueous fluids, in particular, colored biological fluids such as whole blood and urine and biological fluid derivatives such as serum and plasma, is of ever-increasing importance. Important applications exist in medical diagnosis and treatment and in the quantification of exposure to therapeutic drugs, intoxicants, hazardous chemicals, and the like. In some instances, the amounts of materials being determined are either so minuscule—in the range of a milligram or less per deciliter—or so difficult to precisely determine that the apparatus employed is complicated and useful only to skilled laboratory personnel. In this case, the results are generally not available for some hours or days after sampling. In other instances, there is often an emphasis on the ability of lay operators to perform the test routinely, quickly, and reproducibly outside a laboratory setting with rapid or immediate information display.

One common medical test is the measurement of blood glucose levels of diabetics. Current teaching counsels diabetic patients to measure their blood glucose level from two to seven times a day, depending on the nature and severity of their particular cases. Based on the observed pattern in the measured glucose levels, the patient and physician together make adjustments in diet, exercise, and insulin intake to better manage the disease. Clearly, this information should be available to the patient immediately.

Many blood glucose test methods and test articles are known in the art; these all suffer from a variety of limitations. A great improvement is disclosed and claimed in U.S. Pat. Nos. 4,935,346, 5,049,487, 5,059,394 and 5,179,005 by R. Phillips et al. and as assigned to the same assignee as the present application.

The method disclosed and claimed in these patents involves taking a reflectance reading from one surface of an inert porous matrix impregnated with a reagent that will interact with the analyte to produce a light-absorbing reaction product when the fluid being analyzed is applied to another surface and migrates through the matrix to the surface being read. The reagent includes glucose oxidase, an enzyme which consumes glucose in the sample to produce hydrogen peroxide which, in the presence of another enzyme, horseradish peroxidase, oxidizes a dye couple comprising 3-methyl-2-benzothiazolinone hydrazone hydrochloride (MBTH) and 3-dimethylaminobenzoic acid (DMAB) to yield a blue dye. Reflectance measurements are then made at two separate wavelengths. The concentration of the glucose in blood is determined based on the intensity of the dye color with the aid of a LED spectrophotometer.

In my commonly assigned U.S. Ser. No. 245,940, filed May 19, 1994, now U.S. Pat. No. 5,453,360, (LFS 30), there is disclosed a dye couple comprising 3-methyl-2-benzothiazolinone hydrazone in free form or in acid form (MBTH) and 8-anilino-1-napthalenesulfonate, in acid or salt form (ANS) to be used in place of the MBTH-DMAB dye couple as described above. The MBTH-ANS dye couple is less soluble upon oxidation and, hence, provides a more stable endpoint, with minimal dye fading, as compared to the oxidized MBTH-DMAB dye couple.

While these prior systems have been effectively employed to produce useful test devices for the determination of the presence or quantity of glucose, several drawbacks have been noted. The test devices in which such dye couples are employed are designed for both home use and for professional use and as such are sold by the manufacturers and distributors with the expectations that they will remain in the inventory of the user for a substantial period of time and must, of course, remain effective over this period of time. This need for a substantial shelf life has caused difficulties in the formulation of products employing MBTH as one of the components of a dye couple.

Firstly, it has been found that the stability of MBTH decreases with increasing temperature and alkalinity. The acid free form of MBTH is very labile and tends to sublime away. In an attempt to counter this, a preferred form is the acid hydrate of MBTH e.g., 3-methyl-2-benzothiazolinone hydrazone hydrochloride. Unfortunately, this hydrate is itself instable upon increasing temperature and readily dissociates into acid free MBTH and HCl upon heating. In additional to having low stability at high pH, the efficiency of MBTH to oxidatively react with its coupling partner greatly decreases with increasing alkalinities so that at high pH essentially little or no color is produced from the dye couple.

In view of these relationships, in practice MBTH must be used in large excesses and at low pH to minimize the effects of instability and inefficiency. Ideally, a pH of below 2.0 would be preferred from the point of view of low sublimation and high efficiency of the compound. Unfortunately, for the systems being considered herein such an ideal low pH cannot be employed. As described above, the reagent systems employed depend upon enzymes to act on the substrate analyte and generate oxidation agents in quantities indicative of the quantities of the analyte present in the sample being tested. The low pH, which would be ideal with respect to the MBTH reagent, is entirely unsuitable for enzymes such as, for example, glucose oxidase and horseradish peroxidase. At such low pHs many of such commercially available enzymes have little or no activity. Accordingly, the art has been forced to comprise and chose a moderate pH e.g., 4, and a great excess of reagents to insure efficiency of their test devices for the required shelf life.

SUMMARY OF THE INVENTION

In accordance with the teachings of this invention, a highly stable component of a dye couple is provided in a test device containing enzymes. The component, in contrast to those employed in prior test devices, is capable of efficient oxidative coupling with a wide variety of coupling partners at the relatively high pH conditions compatible with high enzyme efficiency.

Specifically, the dye couple compound of this invention is to be used in a test device containing a reagent system for detecting the presence or quantity of an analyte in a sample wherein the reagent system comprises one or more enzymes which, in the presence of the analyte, produce an oxidizing agent in quantities indicative of the quantity of the analyte in the sample. In accordance with the teachings herein, the reagent system further comprises a dye couple capable of forming a chromophore upon being oxidized by the produced oxidizing agent; the dye couple comprises the compound:

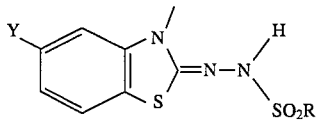

wherein R is selected from the group consisting of alkyl, substituted alkyl, aryl, substituted aryl, heterocyclic, quaternary amine or organic acid moieties and Y is selected from the group consisting of $NO_2$, $SO_3-$, H, halide, alkyl or $SiZ_3$ wherein Z is either alkyl or aryl. Preferably, Y is H. In a preferred embodiment R is:

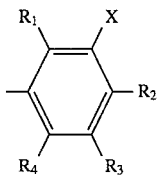

wherein any of $R_1$, $R_2$ and $R_3$ are independently selected from the group consisting of H, alkyl, aryl, silyl, halide, hydroxide, mercaptide, alkoxide, thioalkoxide, amine, sulfonate or carboxylate; and X is selected from the group consisting of amine, sulfonate or carboxylate. In a specific embodiment, the test device is provided to determine the presence or quantity of analytes such as glucose, cholesterol, alcohol, uric acid, formaldehyde or glycerol-3-phosphate, all commonly measured blood analytes. In such cases, the enzyme system will comprise enzymes selected from the group consisting of glucose oxidase, cholesterol oxidase, alcohol oxidase, uricase, aldehyde oxidase, and glycerophosphate oxidase; together with peroxidase or inorganic complex which has peroxidase-like activity; e.g., hematin, hemin and tetrakis[sulphophenyl]porphyrin manganese. A peroxidase of choice is horseradish peroxidase.

DETAILED DISCUSSION OF THE INVENTION

Figure 1:
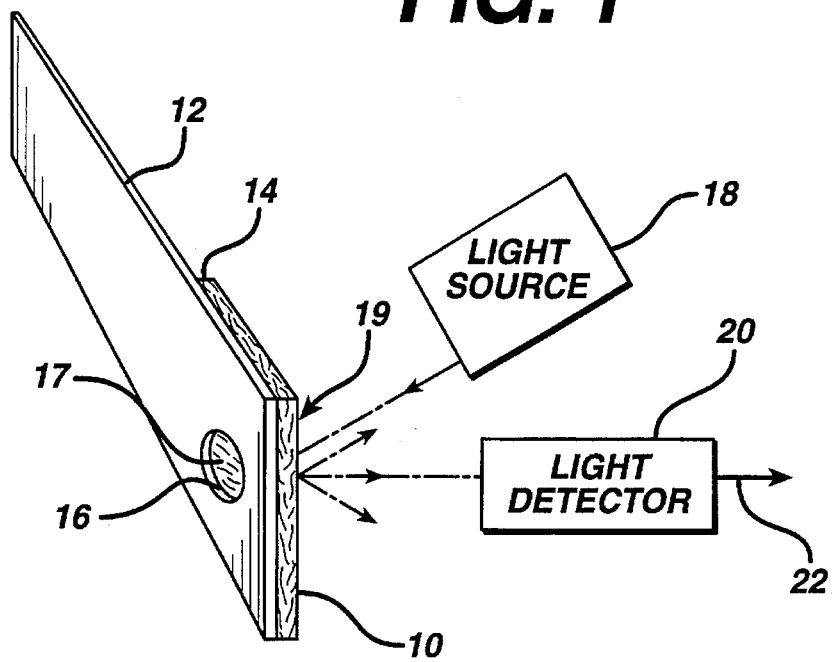
FIG. 1 is a perspective view of one embodiment of a test device containing a reaction pad to which the liquid sample being analyzed is applied.

As described above, the invention involves an improved dye couple compound for use in a test device for determining the presence or quantity of an analyte in a liquid sample. Referring to FIG. 1, in a preferred embodiment of this invention, the test device comprises a porous matrix 10 having incorporated therein a chemical reagent system and being adhered to a support 12. An aperture 16 is provided through the support whereby a liquid sample may be applied to a sample receiving surface 17 of the matrix 10. The chemical system is provided to react with any analyte present in the liquid sample and result in having a test surface 19 of the matrix manifest light reflectance properties indicative of the quantity of analyte present in the liquid sample. The test surface may be read with naked eye, but preferably is read by use of a spectra photo matrix device. Elements of such devices are shown schematically in FIG. 1 and comprise a light source 18 such as a light emitting diode for directing preferably uniform wavelength light onto the test surface 19. Additionally provided is light detector 20 for detecting reflected light from surface 19 and producing a signal 22 indicative of the quantity of detected light, which signal may be processed by, for example, a microprocessor incorporated into the reading apparatus to calculate the quantity of analyte in the sample.

Figure 2:
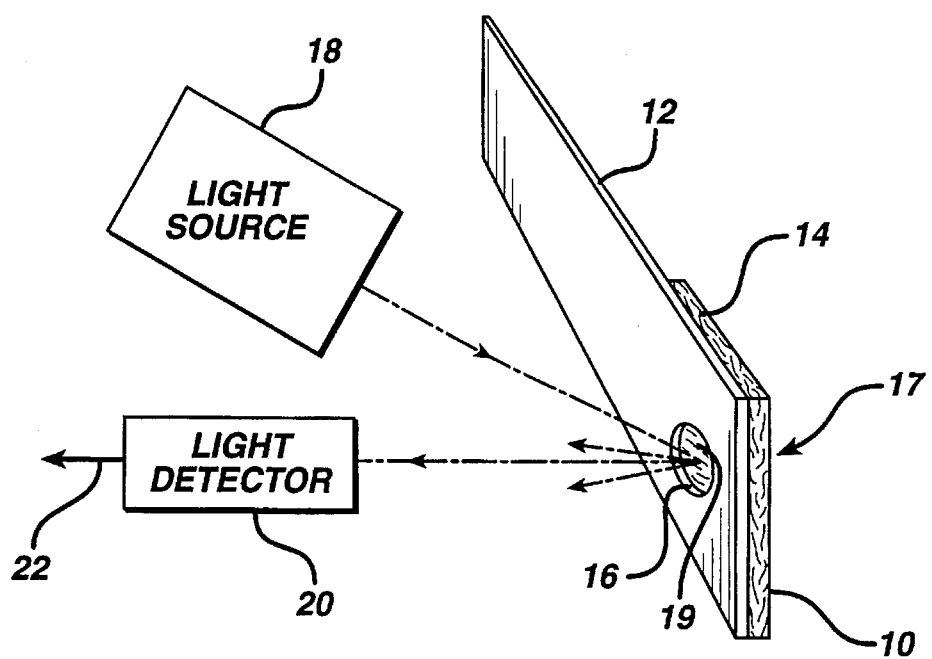
FIG. 2 is a perspective view of a second embodiment of the employment of the test device of FIG. 1.

Systems such as the one described above are now known in the art and are well described in U.S. Pat. Nos. 4,935,346; 5,049,487; 5,059,394; and 5,179,005. Such systems contemplate that these test devices and will be inserted into a reading apparatus and then the sample, e.g., blood, will be applied to the sample receiving surface 17. FIG. 2 represents an alternative to this, wherein blood is first applied to the sample receiving surface 17 and only then is testing surface 19 presented to the apparatus for reading. In all other respects, the numbered elements in FIG. 2 are identical to those of FIG. 1.

The reflectance properties of the testing surface varies with the analyte quantity in the sample by the operation of a series of chemical reactions between the analyte in the liquid sample and the chemical reagents present in the porous matrix. In particular, the matrix includes one or more enzymes which, together with the analyte-substitute, results in the production of hydrogen peroxide or other strong oxidizing agents. A dye couple is included in the matrix; i.e., two compounds which are capable of being oxidized to form a chromophore which absorbs light at specific wave lengths in proportion to the quantity of chromophore present. The oxidizing agent formed by the enzyme catalyzed reaction then reacts with the dye sample to produce the chromophore.

The choice of enzymes, the resulting oxidizing agent and the choice of dye couple vary widely in the art, and are, to a great measure, a function of which analyte is being determined. For example, in the case of determination of cholesterol as in a blood sample, an oxidase enzyme such as cholesterol oxidase may be employed. Similarly, methanol or ethanol determination may employ alcohol oxidase; formaldehyde determinations may employ aldehyde oxidase; or glycerol-3-phosphate determinations may employ glycerophosphate oxidase. The hydrogen peroxide product of these enzyme catalyzed reactions may be further modified by a subsequently enzyme catalyzed reaction to produce an active oxidizing agent for reacting with the dye couple to form the chromophore. Thus, for example, the reaction of hydrogen peroxide to form an active oxidizing reagent may be catalyzed by the enzyme horseradish peroxidase.

Accordingly, while it will be understood that the teachings of this invention are widely applicable, for the purpose of the following discussion, the analyte will be exemplified by glucose in a liquid sample of whole blood. The preferred chemical system will then be exemplified by the enzyme glucose oxidase which acts on the glucose substrate to form hydrogen peroxide. Hydrogen peroxide, in turn, is converted into active oxidizing reagent by the reaction of another enzyme, horseradish peroxidase.

Heretofore, the dye couple widely employed in a diagnostic test for glucose of the kind described above was the combination of 3-methyl-2-benzothiazolinone hydrazone, hydrochloride hydrate (MBTH hydrochloride hydrate) (Formula I) together with dimethylamino benzene (Formula II). These compounds undergo the following oxidization reaction to form a blue colored chromophore (Formula III):

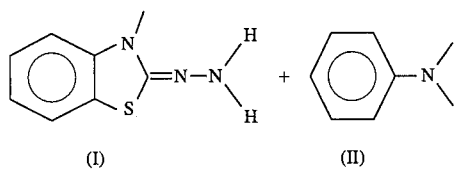

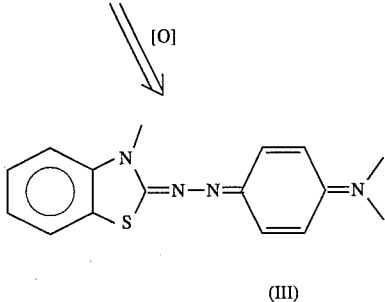

[O] = hydrogen peroxide/horseradish peroxidase

As described above, this system suffers from several drawbacks. The MBTH, even in the hydrochloride hydrate form, is relatively unstable under the action of heat and alkalinity. Furthermore, the above reaction is most efficient under highly acidic conditions; e.g., pH of 2 or less. Unfortunately, at these conditions, the enzymes employed in the test devices e.g., glucose oxidase and horseradish peroxidase, have little or no activity. Accordingly, commercial practice has dictated that in order to get a relatively stable system, an optimum pH is employed; e.g., about 4, and large quantities of both enzymes and the dye couple are used to make up for the decreased activity of the enzymes and the reduced efficiency of the oxidization of the coupling reaction.

In accordance with this invention, it has now been discovered that modified forms of MBTH may be provided which overcome the stability problem heretofore encountered and moreover are efficiently reactive in an environment more conducive to the activity of the enzymes employed in the test devices contemplated herein; e.g., at pH values ranging from about 4 to about 7. Certain preferred derivatives have, moreover, been found to be highly reactive with the desirable coupling partners the aromatic amines. The derivatives of the invention have the general structure set out in Formula IV, below:

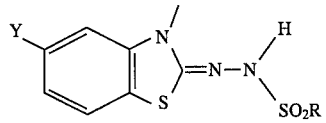

wherein R is selected from the group consisting of alkyl, substituted alkyl, aryl, substituted aryl, heterocyclic, quaternary amine or organic acid moieties and Y is selected from the group consisting of $NO_2$, $SO_3$—,H, halide, alkyl or $SiZ_3$, wherein Z is either alkyl or aryl. Preferably, Y is H. In a preferred embodiment R is:

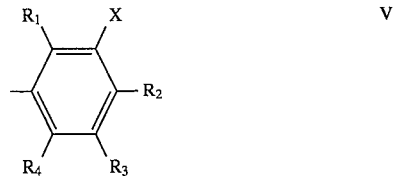

wherein any of $R_1$, $R_2$, $R_3$, and $R_4$ are independently selected from the group consisting of H, alkyl, aryl, silyl, halide, hydroxide, mercaptide, alkoxide, thioalkoxide, amine, sulfonate or carboxylate; and X is selected from the group consisting of amine, sulfonate or carboxylate.

The MBTH derivatives of this invention can undergo an oxidative reaction with a wide range of dye couple partners such as aromatic amines, phenols, and substituted phenols. Moreover, such reactions can proceed efficiently at room temperature and at pHs which may vary from 4 to 11. In the preferred form of the derivatives of this invention, the oxidation reaction is optimal at pHs of from about 4 to about 7 and, hence, is particularly useful in conjunction with the amine dye couple partners of interest in diagnostic chemistry such as 3-dimethylamino benzoic acid and 8-anilino-1-naphthalenesulfonates.

Unlike the MBTH, either in the acid free or in acid hydrate form, these derivatives are remarkably stable even when heated at 100° C. for as much as 16 hours. Moreover, at the conditions of the oxidization reaction, the peroxide catalyzing enzymes, such as horseradish peroxide, are especially effective in turning over the oxidization coupling reaction.

EXAMPLE 1

Synthesis of the MBTH Derivative

Synthesis of meta [3-methyl 2-benzothiazolinone hydrazone]N-sulfonyl benzenesulfonate monosodium, [2]

Synthesis Scheme

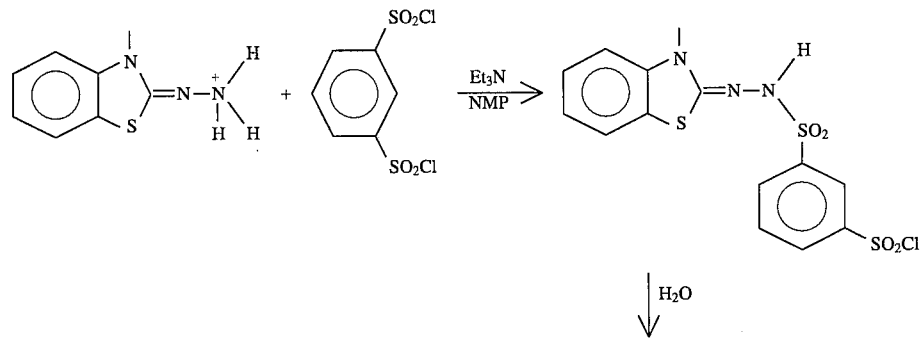

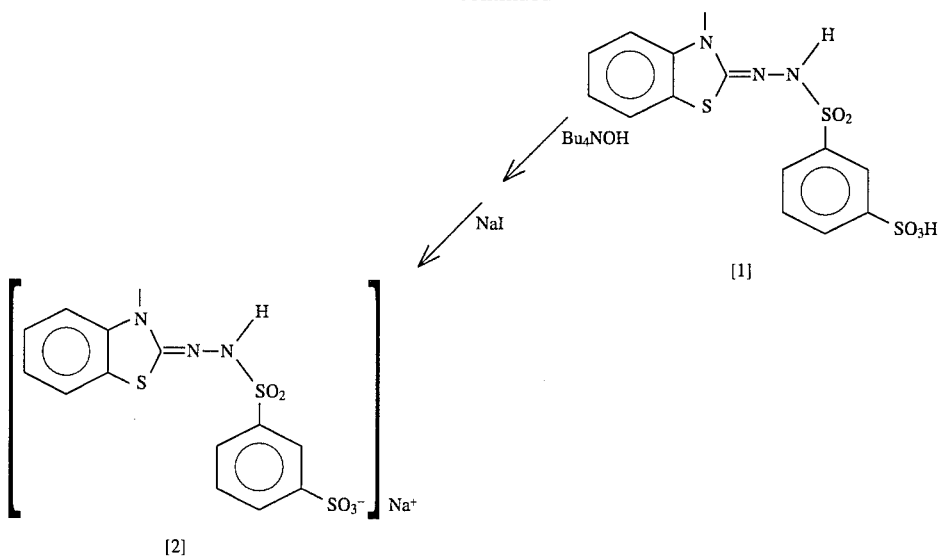

Material 3-methyl 2-benzothiazolinone hydrazone hydrochloride (MBTH.HCl), NaI, tetrabutylammonium hydroxide, methylene chloride and n-methyl-2-pyrrolidone were purchased from the Aldrich Company of Milwaukee, Wis. and used without purification. Triethylamine was obtained from Baker Chemicals and distributed by Baxter Company of Phillipsburg, N.J. The 1,3 disulfonylchloride benzene was purchased from Fluka Chemicals of Ronkonkoma, N.Y. or Lancaster Chemicals of Windham, N.H.

Synthesis of [1]

A 4 gm sample of MBTH.HCl was charged into a 150 ml Erlenmeyer flask equipped with a magnetic stirring bar, and 50 ml of n-methyl-2-pyrrolidone and 5 ml of triethylamine were added. The flask was capped with a rubber septum and placed on a magnetic stirring hot plate. The mixture was heated to 60°–70° C. while stirring vigorously for 0.5 hr., yielding a yellow slurry. The flask was placed into an ice bath to cool.

A 5 gm sample of 1,3 disulfonylchloride benzene was added to a 250 ml Erlenmeyer flask equipped with a magnetic stirring bar. The flask was lowered into an ice bath, and 20 ml of n-methyl-2-pyrrolidone was added. The mixture was stirred until all the solid was dissolved. (ca. 15 min.) The MBTH free-base slurry, which was obtained previously, was decanted into the solution. The resulting light-yellow mixture was allowed to react at an ice-bath temperature for 1.5 hr. After which time, the reaction was quenched with 10 ml of 2N HCl, and it was stirred for an additional 30 min. at room temperature. 50 mg of 12 mesh Norti (activated carbon pellets) was introduced to the solution, affording a light yellow solution after 10 min of stirring. It was then filtered through a fine graded frit with the aid of an aspirator. A yellow to light brown smooth solution was obtained. 300 ml of 2N HCl was added to the stirring yellow solution, resulting in precipitation of an off-white powder. The solid was collected via vacuum filtration and the product was washed 3 times with 25 ml deionized water. Upon drying at 110° C. in vacuum for 2 hr. 5.6 gm of the off-white product was obtained. The product was analyzed with $^1$H NMR and HPLC to be 97% pure.

Compound [1] is not very soluble in most of the common organic solvents and water. It is, however, soluble in basic solution and polar solvents, such as DMSO, NMP and DMF.

Synthesis of [2]

A 2.0 gm sample of the crude [1] was suspended in 50 ml methylene chloride. 4 ml of 1M tetrabutylammonium hydroxide was added slowly, in a course of 2 min, to the stirring suspension; affording a light yellow solution. The solution was washed with 10 ml deionized water and dried over anhydrous sodium sulfate. The sulfate was removed via gravity filtration, and the resulting mixture was evaporated to dryness with a rotary-evaporator. A thick yellow oil was collected. The oil was taken up with 125 ml acetone, and 10 ml of 20% NaI in acetone was added in the course of 5 min. A white precipitant was apparent. The mixture was allowed to react for an additional 20 min., and the precipitant was collected via vacuum filtration with a fine-grade frit. The resulting off-white solid was washed 3 times with 20 ml acetone. Upon drying at 110° C. for 45 min, 1.3 grm (65%) of the desired product was obtained.

Compound [2] is very soluble in water and in a water-alcohol mixture. The solid is stable in air and light, but its solution decomposes slowly to a light yellow hazy mixture when exposed to light for a prolonged period of time.

EXAMPLE 2

Preparation of a Test Device

A strip of polymer membrane (reaction matrix) is submerged into the aqueous dip in Table 1 until saturated. It is removed from the dip and the excess reagent is squeegeed off with a glass rod. The strip is then hung inside an air circulating over at 56° C. for about 5–10 minutes to dry, after which time the strip is removed and dipped into the organic dip described in Table 1 until saturated. Again, it is then dried as in the previous step. The resulting strip is fashioned into a desired shape for testing.

TABLE 1

Formulation of Reagents

| Aqueous Dip (Adjust pH to 4.25 with NaOH) | | Organic Dip | |
|---|---|---|---|
| Water | 20 ml | Water | 3 ml |
| Citric acid | 420 mg | Denatured Alcohol | 7 ml |
| Ethylene diamine tetraacetic acid (EDTA) | 16.7 mg | Meta[3-methyl 2-benzothiazolinone hydrazone N-sulfonyl benzenesulfonate monosodium [2] | 10–60 mg |
| Gantrez S95 (available from GAF, New York, New York | 90 mg | ANS | 10–100– mg |
| Crotein SPA (available from Croda Co., New York, New York | 250 mg | | |
| Glucose oxidase | 20,500 units | | |
| Horseradish peroxidase | 16,200 units | | |

EXAMPLE 3

Determination of Glucose

A glucose containing blood sample is applied onto the surface of the reagent impregnated strip. The sample is immediately absorbed into the matrix and a blue color is apparent. The intensity of color increases with time and is proportional to the concentration of analyte. Based on the color intensity, the glucose concentration is determined by comparing with a standard calibration curve.

Similarly, an aqueous solution of hydrogen peroxide (organic peroxides, ferric and quinone) also produces the desired blue color on the reagent impregnated strip. The concentration of the analyte may be determined by the same means as above.

The invention now being fully described, it will be apparent to one of ordinary skill in the art that any modifications and changes may be made thereto without departing from the spirit and scope of the present invention.

What is claimed is:

1. In a test device containing a reagent system for determining the presence or quantity of an analyte in a sample wherein said reagent system comprises enzymes to produce an oxidizing agent in quantities indicative of quantities of said analyte in said sample; the improvement wherein:

said reagent system comprises a dye couple forming a chromophore upon being oxidized by said oxidizing agent at pH less than about 11, said dye couple comprising a compound having the formula:

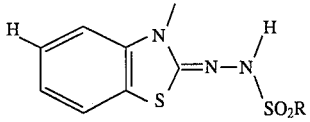

wherein R is selected from the group consisting of alkyl, substituted alkyl, aryl, substituted aryl, heterocyclic, quaternary amine or organic add moieties.

2. The test device of claim 1 wherein R is:

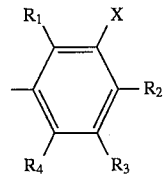

wherein any of $R_1$, $R_2$, $R_3$, and $R_4$ are independently selected from the group consisting of H, alkyl, aryl, silyl, halide, hydroxide, mercaptide, alkoxide, thioalkoxide, amine, sulfonate or carboxylate; and X is selected from the group consisting of amine, sulfonate or carboxylate.

3. The test device of claim 1 wherein said enzymes are selected from the group consisting of glucose oxidase, cholesterol oxidase, alcohol oxidase, uricase, aldehyde oxidase, and glycerophosphate oxidase.

4. The test device of claim 3 wherein said enzymes further comprise peroxidase or inorganic complex having peroxidase properties.

5. The test device of claim 3 wherein said enzymes comprise glucose oxidase and horseradish peroxidase.

6. The test device of claim 1 wherein said dye couple further comprises 3-dimethylaminobenzoic acid.

7. The test device of claim 1 wherein said dye couple further comprises 8-anilino-1-naphthalenesulfonate.

8. The test device of claim 1 wherein said compound is meta[3-methyl 2-benzothiazolinone hydrozone]N-sulfonyl benzenesulfonate monosodium.

\* \* \* \* \*